(12) United States Patent
Haynie et al.

(10) Patent No.: US 7,662,911 B2
(45) Date of Patent: Feb. 16, 2010

(54) POLYPEPTIDE FILMS AND METHODS

(75) Inventors: Donald T. Haynie, New Haven, CT (US); Zheng-liang Zhi, Liverpool (GB)

(73) Assignee: Louisiana Tech University Research Foundation, Ruston, LA (US)

( * ) Notice: Subject to any disclaimer, the term of this patent is extended or adjusted under 35 U.S.C. 154(b) by 459 days.

(21) Appl. No.: 11/559,175

(22) Filed: Nov. 13, 2006

(65) Prior Publication Data

US 2007/0207212 A1 Sep. 6, 2007

Related U.S. Application Data

(60) Provisional application No. 60/736,723, filed on Nov. 14, 2005.

(51) Int. Cl.
*C07K 17/00* (2006.01)

(52) U.S. Cl. ....................................... 530/300

(58) Field of Classification Search ........................ None
See application file for complete search history.

(56) References Cited

U.S. PATENT DOCUMENTS

| | | |
|---|---|---|
| 6,479,146 B1 | 11/2002 | Caruso et al. |
| 6,743,521 B2 | 6/2004 | Hubbell et al. |
| 6,833,192 B1 | 12/2004 | Caruso et al. |
| 7,321,022 B2 * | 1/2008 | Haynie ........................ 530/300 |
| 7,348,399 B2 * | 3/2008 | Haynie ........................ 530/300 |
| 7,411,038 B2 * | 8/2008 | Haynie ........................ 530/300 |
| 2004/0013721 A1 | 1/2004 | Antipov et al. |
| 2004/0014073 A1 | 1/2004 | Trau et al. |
| 2004/0241202 A1 | 12/2004 | Chluba et al. |
| 2005/0069950 A1 | 3/2005 | Haynie |
| 2006/0147543 A1 * | 7/2006 | Haynie ........................ 424/490 |
| 2006/0205005 A1 * | 9/2006 | Haynie ........................... 435/6 |
| 2007/0077253 A1 * | 4/2007 | Haynie .................... 424/184.1 |
| 2007/0077275 A1 * | 4/2007 | Haynie ........................ 424/423 |
| 2007/0077276 A1 * | 4/2007 | Haynie ........................ 424/423 |
| 2008/0125575 A1 * | 5/2008 | Haynie ........................ 530/324 |
| 2009/0054633 A1 * | 2/2009 | Haynie ........................ 530/402 |

FOREIGN PATENT DOCUMENTS

WO 9308766 5/1993

OTHER PUBLICATIONS

Balabushevich et al. ("Fabrication and Characterization of Polyelectrolyte Microparticles with Protein," Biochemistry (Moscow), 2004, 69, 757-762, translated from Biokhimiya, 2004, 69, 930-936, Originally published in Biochemistry (Moscow), On-Line Papers in Press, as Manuscript BM03_275, Mar. 28, 2004).*
Radtchenko et al. ("Incorporation of macromolecules into polyelectrolyte micro and nanocapsules via surface controlled precipitation on colloidal particles," Colloids and Surfaces A: Physicochemical and Engineering Aspects, 2002, 202, 127-133).*
Rillings et al. ("Encapsulation of cytochrome C by multilayer microcapsules. A model for improved enzyme immobilization," Journal of Membrane Science, 1997, 129, 283-287).*
Shenoy et al. ("Microgel-Based Engineered Nanostructures and Their Applicability with Template-Directed Layer-by-Layer Polyelectrolyte Assembly in Protein Encapsulation," Macromol. Biosci. 2005, 5, 451-458).*
Sutherland-Smith et al. ("Crystal Structure of a Human Embryonic Haemoglobin: The Carbonmonoxy Form of Gower ll ( 2 2) Haemoglobin at 2.9 A Resolution," J. Mol. Biol., 1998, 280, 475-484).*
Decher, Gero; "Fuzzy Nanoassemblies: Toward Layered Polymeric Multicomposites" Science; 277; pp. 1232-1237; (1997).
Iler, R.K.; "Multilayers of Collodial Particles"; Journal of Colloid and Interface Science; 21, pp. 569-594; (1966).
Lvov, Y. "Electrostatic Layer-by-Layer Assembly of Proteins and Polyions"; in Protein Architecture: Interfacing Molecular Assemblies and Immobilization Biotechnology; New York; Marcel Dekker, Edr.; pp. 125-167; ISBN: 0824782364; (1999).
Lvov, Y.; "Urease Encapsulation in Nanoorganized Microshells"; Nano Letters; 1; pp. 125-128; (2001).
Patel et al; "Polymeric Precipitants for the Crystallization of Macromolecules"; Biochemical and Biophysical Research Communications; 207; pp. 819-828; (Feb. 15, 1995).
Peyratout, et al; "Tailor-Made Polyelectrolyte Microcapsules: From Multilayers to Smart Containers"; Angew. Chem. Int. Ed.; 43; pp. 3762-3783; (2004).
International Search Report and Written Opinion; International Application No. PCT/US2006/043986; International Filing Date Nov. 13, 2006; Applicant's File Reference ATE0005PCT; Date of Mailing Jun. 13, 2008; 12 pages.

* cited by examiner

*Primary Examiner*—Cecilia Tsang
*Assistant Examiner*—Christina Bradley
(74) *Attorney, Agent, or Firm*—Cantor Colburn LLP

(57) ABSTRACT

Disclosed herein is a method of making a film, the method comprising depositing a first layer polyelectrolyte on a surface of a substrate to form a first layer; and depositing a second layer polyelectrolyte on the first layer polyelectrolyte to form a second layer. The first layer polyelectrolyte, the second layer polyelectrolyte, or both, is deposited on the substrate in the presence of a polymeric precipitant; and the first layer polyelectrolyte and the second layer polyelectrolyte have net charges of opposite polarity. Also disclosed are methods of improving bioactive molecule retention during fabrication of a polyelectrolyte multilayer film.

20 Claims, 7 Drawing Sheets

Figure 1

Layer-by-Layer Self-Assembly (LBL) of Multilayer Films

Film Formed on a Planar Substrate (Coating)

Film Formed on a Spherical Template (Capsule)

Figure 7

# POLYPEPTIDE FILMS AND METHODS

CROSS-REFERENCE TO RELATED APPLICATION

This application claims the benefit of U.S. Provisional Application No. 60/736,723, filed Nov. 14, 2005, which is incorporated by reference herein.

TECHNICAL FIELD

The present invention relates to the fabrication of nanoengineered polypeptide films and microcapsules, and methods for making and using such films and microcapsules. More specifically, the present invention relates to the encapsulation of functional biomacromolecules in nanoengineered polypeptide microcapsules.

BACKGROUND

Figure 1:
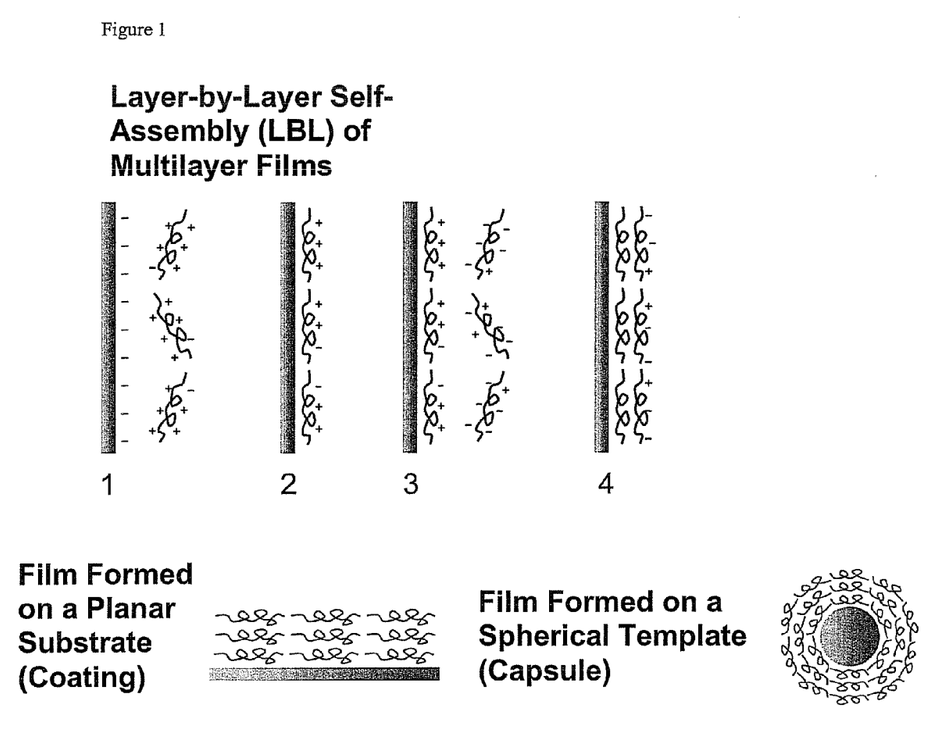
FIG. 1 shows a schematic of the assembly of oppositely charged polypeptides.

Polyelectrolyte multilayer films are thin films (e.g., a few nanometers to millimeters thick) composed of alternating layers of oppositely charged polyelectrolytes. Such films can be formed by layer-by-layer assembly onto a suitable substrate. In electrostatic layer-by-layer self-assembly ("ELBL"), the physical basis of association of polyelectrolytes is electrostatics. Film buildup is possible because the sign of the surface charge density of the film reverses on deposition of successive layers. The general principle of ELBL deposition of oppositely charged polyions is illustrated in FIG. 1. The generality and relative simplicity of the ELBL film process permits the deposition of many different types of polyelectrolytes onto many different types of surface. Polypeptide multilayer films are a subset of polyelectrolyte multilayer films, comprising at least one layer comprising a charged polypeptide. A key advantage of polypeptide multilayer films is environmental benignity. ELBL films can also be used for encapsulation. Applications of polypeptide films and microcapsules include, for example, nano-reactors, biosensors, artificial cells, and drug delivery vehicles.

The design principles for incorporation of polypeptides into multilayer films were first elucidated in U.S. Patent Publication No. 20050069950. In brief, the suitability of a polypeptide for ELBL is related to the net charge on the polypeptide and the length of the polypeptide. A polypeptide suitable for ELBL preferably comprises one or more amino acid sequence motifs, that is, contiguous amino acid sequences having a length of about 5 to about 15 amino acid residues and having a suitable linear charge density for electrostatic deposition. A polypeptide for ELBL can be designed in different ways, for example, by joining a plurality of amino acid sequence motifs to each other, either directly, or by a linker. Polypeptides having the appropriate length and charge properties can readily be deposited to form one or more layers of a polypeptide multilayer film.

Proteins, peptides, and oligonucleotides can be potent therapeutic agents. Such biomolecules, however, are targets of various degradation mechanisms in vivo. Encapsulation of biomolecules and other bioactive molecules within a biocompatible microenvironment, for extended preservation of function or controlled release, is a strategy for improving the availability of the bioactive molecules at targeted sites. Deposition of a polypeptide film over a substrate coated with a biomolecule could similarly extend preservation of function or control release of the biomolecule. Electrostatic layer-by-layer nanoassembly is one means of preparing polyelectrolyte multilayer films and microcapsules of high stability and tunable permeability.

There remains a need for alternative means of achieving direct and efficient retention of functional bioactive macromolecules, for example a protein, in engineered biodegradable polypeptide films and microcapsules.

SUMMARY

In one embodiment, a method of making a film comprises depositing a first layer polyelectrolyte on a surface of a substrate to form a first layer; and depositing a second layer polyelectrolyte on the first layer polyelectrolyte to form a second layer. The first layer polyelectrolyte, the second layer polyelectrolyte, or both, is deposited on the substrate in the presence of a polymeric precipitant; and the first layer polyelectrolyte and the second layer polyelectrolyte have net charges of opposite polarity. In another embodiment, the first layer polyelectrolyte, the second layer polyelectrolyte, or both, comprise a homopolypeptide of lysine, glutamic acid, or another amino acid type that has a charged side chain at neutral pH. In another embodiment, the first layer polyelectrolyte, the second layer polyelectrolyte, or both, comprises a designed polypeptide, wherein the designed polypeptide comprises one or more first amino acid sequence motifs, wherein the one or more first amino acid sequence motifs consists of 5 to 15 amino acid residues and has a magnitude of net charge per residue of greater than or equal to 0.4, and wherein the designed polypeptide is not a homopolypeptide, is at least 15 amino acid residues long, and has a magnitude of net charge per residue of greater than or equal to 0.4.

In another embodiment, a method of improving bioactive molecule retention during fabrication of a polyelectrolyte multilayer film comprises depositing a first layer polyelectrolyte on a surface of a substrate to form a first layer; and depositing a second layer polyelectrolyte on the first layer polyelectrolyte to form a second layer. The first layer polyelectrolyte, the second layer polyelectrolyte, or both, is deposited on the substrate in the presence of a polymeric precipitant; the first layer polyelectrolyte and the second layer polyelectrolyte have net charges of opposite polarity; and the substrate comprises a bioactive molecule.

The above described and other features are exemplified by the following figures and detailed description.

DRAWINGS

Referring now to the figures, which are exemplary embodiments.

DETAILED DESCRIPTION

The present invention is directed to polyelectrolyte multilayer films and in particular, a novel method for making the films. In one embodiment, the films comprise a bioactive molecule. In another embodiment, the polyelectrolyte multilayer films comprise one or more polypeptide layers.

As used herein, "layer" means a thickness increment, e.g., on a substrate for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments.

The term "polyelectrolyte" includes polycationic and polyanionic materials having a molecular weight of greater than 1,000 and at least 5 charges per molecule. Suitable polycationic materials include, for example, polyamines. Polyamines include, for example, a polypeptide, polyvinyl amine, poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl aminomethacrylate), poly(N-ethyl aminomethacrylate), poly(N,N-dim ethyl aminomethacrylate), poly(N,N-diethyl aminomethacrylate), poly(ethyleneimine), poly(diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide, a nucleic acid, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials.

"Amino acid" means a building block of a polypeptide. As used herein, "amino acid" includes the 20 common naturally occurring L-amino acids, all other natural amino acids, all non-natural amino acids, and all amino acid mimics, e.g., peptoids.

"Naturally occurring amino acid" means the 20 common naturally occurring L-amino acids, that is, glycine, alanine, valine, leucine, isoleucine, serine, threonine, cysteine, methionine, aspartic acid, asparagine, glutamic acid, glutamine, arginine, lysine, histidine, phenylalanine, tyrosine, tryptophan, and proline.

"Non-natural amino acid" means an amino acid other than any of the 20 common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the α-carbons of the residue. Consequently, the chemical linkages between monomers in a polypeptoid are not peptide bonds, which can be useful for limiting proteolytic digestion.

"Amino acid sequence" and "sequence" mean a contiguous length of polypeptide chain that is at least two amino acid residues long.

"Residue" means an amino acid in a polymer or oligomer; it is the residue of the amino acid monomer from which the polymer was formed. Polypeptide synthesis involves dehydration, that is, a single water molecule is "lost" on addition of the amino acid to a polypeptide chain.

"Amino acid sequence motif" means a contiguous amino acid sequence comprising n residues, wherein n is 5 to 15. In one embodiment, the magnitude of the net charge per residue of an amino acid sequence motif is greater than or equal to 0.4. In another embodiment, the magnitude of the net charge per residue of an amino acid sequence motif is greater than or equal to 0.5. As used herein, the magnitude of the net charge refers to the absolute value of the net charge, that is, the net charge can be positive of negative.

"Designed polypeptide" means a polypeptide comprising one or more amino acid sequence motifs, wherein the polypeptide is at least 15 amino acids in length and the ratio of the number of charged residues of the same polarity minus the number of residues of the opposite polarity to the total number of residues in the polypeptide is greater than or equal to 0.4 at pH 7.0. In other words, the magnitude of the net charge per residue of the polypeptide is greater than or equal to 0.4. In one embodiment, the ratio of the number of charged residues of the same polarity minus the number of residues of the opposite polarity to the total number of residues in the polypeptide is greater than or equal to 0.5 at pH 7.0. In other words, the magnitude of the net charge per residue of the polypeptide is greater than or equal to 0.5. While there is no absolute upper limit on the length of the polypeptide, in general, designed polypeptides suitable for ELBL deposition have a practical upper length limit of 1,000 residues.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include α helix, β sheet, and β turn.

"Polypeptide multilayer film" means a film comprising one or more polypeptides such as the designed polypeptides defined above. For example, a polypeptide multilayer film comprises a first layer comprising a designed polypeptide and a second layer comprising a polyelectrolyte have a net charge of opposite polarity to the designed polypeptide. For example, if the first layer has a net positive charge, the second layer has a net negative charge; and if the first layer has a net negative charge, the second layer has a net positive charge. The second layer comprises another designed polypeptide or another polyelectrolyte.

"Substrate" means a solid material with a suitable surface for adsorption of polyelectrolytes from aqueous solution. The surface of a substrate can have essentially any shape, for example, planar, spherical, rod-shaped, and the like. Substrate surface are regular or irregular. A substrate can be a crystal. A substrate optionally includes bioactive molecules. Substrates range in size from the nanoscale to the macroscale. Moreover, a substrate optionally comprises several small sub-particles. A substrate can be made of organic material, inorganic material, bioactive material, or a combination thereof. Nonlimiting examples of substrates include silicon wafers; charged colloidal particles, e.g., microparticles of CaCO₃ or of melamine formaldehyde; protein crystals; nucleic acid crystals; drug crystals; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "microcapsule" is a polyelectrolyte film in the form of a hollow shell or a coating surrounding a core. The term core thus means the interior of a microcapsule. The core comprises a variety of different encapsulants, such as a protein, a drug, or a combination thereof, in liquid or crystalline form, for example.

"Bioactive molecule" means a molecule, macromolecule, or macromolecular assembly having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film is a transplanted islet cell, a eukaryotic cell, a bacterial cell, a plant cell, and a yeast cell.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an antigen is an entity that elicits an immune response. The human body fights infection and inhibits reinfection by increasing the number of antibodies in the bloodstream and elsewhere. The specific immune response depends somewhat on the individual, though general patterns of response are the norm.

"Epitope" means the structure or sequence of a protein that is recognized by an antibody. Ordinarily an epitope will be on the surface of a protein. A "continuous epitope" is one that involves several contiguous amino acid residues, not one that involves amino acid residues that happen to be in contact or in the limited region of space in a folded protein.

"Polymeric precipitant" means a chemical such as a soluble polymer that affects solubility of a bioactive molecule. In one embodiment, a polymeric precipitant means a water soluble polymer that decreases the solubility in water of a bioactive molecule adsorbed on a template and/or the solubility in water of a polyelectrolyte used in fabrication of a film on a template. In aqueous solution, the polymeric precipitant attracts solvent water molecules away from the surface of a bioactive molecule-coated template, effectively decreasing solubility of the bioactive molecule in bulk aqueous solution, and thereby increasing the amount of the bioactive molecule that is retained on the template during the polyelectrolyte film assembly process. The polymeric precipitant can also have a favorable influence on capsule stability during template dissolution by changing the osmotic pressure gradient across the capsule wall.

Nonlimiting examples of a polymeric precipitant are polyethylene glycol (PEG), polyacrylic acid (sodium salt), polyvinyl alcohol (PVA), polyvinylpyrrolidone, polypropylene glycol (PPG), diethylaminoethyldextran, polyethyleneimine (PEI), and combinations comprising one or more of the foregoing polymeric precipitants. The preferred molecular weight of the polymeric precipitant will vary from polymer to polymer. It must be noted that molecular weight is a strong determinant of the solubility of a polymeric precipitant, so that the higher the molecular weight, the lower the solubility. Practical values of molecular weight for some of the mentioned polymers for use as polymeric precipitants of biomacromolecules are 425 Da for PPG, 5,000 Da for PVA, and 40 to 60 kDa for PEI. Further details on the solubility of such polymers are readily available in the scientific literature.

One aspect of the invention disclosed herein provides a method of making a multilayer film. The method comprises depositing a plurality of layers of oppositely charged polyelectrolytes on a substrate. Deposition of at least one of the oppositely charged polyelectrolytes is performed in the presence of a polymeric precipitant. In some embodiments, the deposition is by layer-by-layer assembly (LBL). Successively deposited layers have opposite signs of net charge. In one embodiment, one or more layers comprises a designed polypeptide. In other embodiments, at least one of the oppositely charged polypeptides comprises a homopolypeptide such as poly (L-lysine) or poly (L-glutamic acid).

The design principles for polypeptides suitable for electrostatic layer-by-layer deposition are elucidated in U.S. Patent Publication No. 2005/0069950, incorporated herein by reference. Briefly, the primary design concerns are the length and charge of the polypeptide. Electrostatics is the most important design concern because it is the basis of ELBL. Without suitable charge properties, a polypeptide will not be substantially soluble in aqueous solution at pH 4 to 10 and cannot readily be used for the fabrication of a multilayer film by ELBL. Other design concerns include the physical structure of the polypeptides, the physical stability of the films formed from the polypeptides, and the biocompatibility and bioactivity of the films and the constituent polypeptides.

As defined above, a designed polypeptide means a polypeptide comprising one or more amino acid sequence motifs, wherein the polypeptide is at least 15 amino acid residues in length and the magnitude of the net charge per residue of the polypeptide is greater than or equal to 0.4 at pH 7.0. "Amino acid sequence motif" means a contiguous amino acid sequence comprising n amino acid residues, wherein n is 5 to 15. Positively-charged (basic) naturally-occurring amino acids at pH 7.0 are Arg, H is, and Lys. Negatively-charged (acidic) naturally-occurring amino acid residues at pH 7.0 are Glu and Asp. An amino acid motif comprising a mixture of amino acid residues of opposite charge can be employed so long as the overall ratio of charge meets the specified criteria. In one embodiment, a designed polypeptide is not a homopolypeptide.

In one exemplary embodiment, the amino acid sequence motif comprises 7 amino acid residues. Four charged amino acid residues is a suitable minimum for a motif size of 7, because fewer than 4 charges yields decreased peptide solubility and decreased control over ELBL. Further, regarding biocompatibility, each identified amino acid sequence motif in genomic data is long enough at 7 amino acid residues to constitute a continuous epitope, but not so long as to correspond substantially to residues both on the surface of a protein and in its interior. Thus, the charge and length of the amino acid sequence motif help to ensure that an amino acid sequence motif identified in genomic data is likely to occur on the surface of the folded protein from which the sequence motif is derived. In contrast, a very short motif could appear to the body to be a random sequence, or one not specifically "self", and therefore elicit an immune response.

In some cases, a design concern regarding amino acid sequence motifs and designed polypeptides is their propensity to form secondary structures, notably α helix or β sheet. In some embodiments, it is desirable to be able to control, e.g., minimize, secondary structure formation by the designed polypeptides in an aqueous medium in order to maximize control over thin film layer formation. First, it is preferred that sequence motifs be relatively short, that is about 5 to about 15 amino acid residues, because long motifs are more likely to adopt a stable three-dimensional structure in solution. Second, a linker, such as a glycine or proline residue, covalently joined between successive amino acid sequence motifs in a designed polypeptide will reduce the propensity of the polypeptide to adopt secondary structure in solution. Glycine, for example, has a very low α helix propensity and a very low β sheet propensity, making it energetically very unfavorable for a glycine and its neighboring amino acids to form regular secondary structure in aqueous solution. Third, the α helix and β sheet propensity of the designed polypeptides themselves can be minimized by selecting amino acid sequence motifs for which the summed α helix propensity is less than 7.5 and the summed β sheet propensity is less than 8. "Summed" propensity means the sum of the α helix or β sheet propensities of all amino acids in a motif. Amino acid sequence motifs having a somewhat higher summed α helix propensity and/or summed β sheet propensity are suitable for ELBL, particularly when joined by linkers such as Gly or Pro. In certain applications, the propensity of a polypeptide to form secondary structure can be relatively high as a specific design feature of thin film fabrication. The secondary structure propensities for all 20 naturally occurring amino acids can be calculated using the method of Chou and Fasman (see P. Chou and G. Fasman, *Biochemistry*, 13:211 (1974), which is incorporated by reference herein in its entirety).

Another design concern is control of the stability of polypeptide ELBL films. Ionic bonds, hydrogen bonds, van der Waals interactions, and hydrophobic interactions contribute to the stability of multilayer films. In addition, covalent disulfide bonds formed between sulfhydryl-containing amino acids in the polypeptides within the same layer or in adjacent layers can increase structural strength. Sulfydryl-containing amino acids include cysteine and homocysteine. In addition, a sulfhydryl can be added to β-amino acids such as D,L-β-amino-β-cylohexyl propionic acid; D,L-3-aminobutanoic acid; or 5-(methylthio)-3-aminopentanoic acid. Sulfhydryl-containing amino acids can be used to "lock" (bond together) and "unlock" layers of a multilayer polypeptide film by a change in oxidation potential. Also, the incorporation of a sulfhydryl-containing amino acid in a sequence motif of a designed polypeptide enables the use of relatively short peptides in thin film fabrication, by virtue of intermolecular disulfide bond formation. Amino acid sequence motifs containing sulfhydryl-containing amino acids may be selected from a library of motifs identified using the methods described below, or designed de novo.

In one embodiment, the designed sulfhydryl-containing polypeptides, whether synthesized chemically or produced in a host organism, are assembled by ELBL in the presence of a reducing agent to prevent premature disulfide bond formation. Following film assembly, the reducing agent is removed and an oxidizing agent is added. In the presence of the oxidizing agent disulfide bonds form between sulfhydryls groups, thereby "locking" together the polypeptides within layers and between layers where thiol groups are present. Suitable reducing agents include dithiothreitol ("DTT"), 2-mercaptoethanol (2-ME), reduced glutathione, tris(2-carboxyethyl)phosphine hydrochloride (TCEP), and combinations of more than one of these chemicals. Suitable oxidizing agents include oxidized glutathione, tert-butylhydroperoxide (t-BHP), thimerosal, diamide, 5,5'-dithio-bis-(2-nitro-benzoic acid) (DTNB), 4,4'-dithiodipyridine, sodium bromate, hydrogen peroxide, sodium tetrathionate, porphyrindin, sodium orthoiodosobenzoate, and combinations of more than one of these chemicals.

Biocompatibility is a design concern in biomedical applications. In such applications, genomic or proteomic information is used as a basis for polymer design to yield, ideally, "immune inert" polypeptides. The approach will be particularly useful if the fabricated or coated object will make contact with circulating blood. Because the amino acid sequence motifs are highly polar, they typically occur on the surface of the native folded form of the protein from which they are derived. The "surface" is that part of a folded protein that is in contact with the solvent or inaccessible to the solvent solely because of the granular nature of water. Amino acid sequence motifs identified in blood proteins are effectively always in contact with cells and molecules of the immune system while the protein is in the blood. Therefore, polypeptides derived from the surface of folded blood proteins are less likely to be immunogenic than sequences selected at random. Designed polypeptides will generally be biocompatible, but the extent of immune response or any other type of biological response may well depend on specific details of a sequence motif.

Bioactivity can be incorporated into a film, coating or microcapsule by a number of methods. For example, a designed polypeptide comprising the film can comprise a functional domain. Alternatively, bioactivity may be associated with another bioactive molecule encapsulated or coated by the polypeptide thin film. In one embodiment, the template comprises a bioactive molecule such as a protein crystal.

A functional domain in this context is an independently thermostable region of a protein that has specific biofunctionality (e.g., binding phosphotyrosine). In a multi-domain protein, multiple functional domains may exist, as for example in the protein tensin, which encompasses a phosphotyrosine binding domain and a protein tyrosine phosphatase domain. The inclusion of a functional domain in a designed polypeptide incorporated into a multilayer film can provide the film with a desired functionality, including, for example, specific ligand binding, targeting in vivo, biosensing, and biocatalysis.

The bioactive molecule can be a protein, a functional fragment of a protein, a functional fragment of a protein that is not part of a designed polypeptide, a complex of proteins, an oligopeptide, an oligonucleotide, a nucleic acid, a ribosome, an active therapeutic agent, a phospholipid, a polysaccharide, a lipopolysaccharide, a functional membrane fragment, a membrane structure, a virus, a pathogen, a cell, an aggregate of cells, an organelle, a lipid, a carbohydrate, a pharmaceutical, or an antimicrobial agent. The bioactive molecule can be in the form of a well-ordered or amorphous crystal. The protein can be an enzyme or an antibody. The substrate can comprise the bioactive molecule. In one embodiment, the substrate has a bioactive molecule disposed on its surface prior to deposition of layers of oppositely charged polypeptides. In another embodiment, the substrate is a crystal comprising the bioactive molecule.

In one embodiment, amino acid sequence motifs are designed de novo. In other embodiments, amino acid sequence motifs are selected from the genomic or proteomic information of a specific organism, such as the human genome. For example, the primary structure of complement C3 (gi|68766) or lactotransferrin (gi|4505043) can be used to search for amino acid sequence motifs in a human blood protein.

A method of identifying a first amino acid sequence motif in a polypeptide comprises selecting a starter amino acid residue in the polypeptide; examining an amino acid sequence comprising the starter amino acid residue and the following n−1 amino acid residues in the polypeptide for occurrences of positive and negative charges, wherein n is 5 to 15; determining the 5 to 15 amino acid residues as an amino acid sequence motif if the net charge of the side chains of the 5-15 amino acid residues at pH 7 is greater than or equal to 0.4*n; or discarding the sequence if the net charge of the side chains of the 5-amino acid residues at pH 7 is less than 0.4*n.

In one embodiment, the process of searching protein sequence data for a negatively charged amino acid sequence motif of length n comprising only amino acids that are neutral or negatively charged is described as follows. First, a first amino acid residue is selected in a protein sequence. Second, this amino acid residue and the following n−1 amino acid residues are examined for occurrences of arginine (Arg), histidine (His), or lysine (Lys) (the three naturally occurring amino acids that may be positively charged at neutral pH), where n is 5 to 15. Third, if one or more Arg, His, or Lys residues is found in these n amino acid residues, the process is begun anew at a second amino acid residue. If, however, no Arg, His, or Lys is found in these n residues, the n residues are examined to determine the number of occurrences of glutamate (Glu) and/or aspartate (Asp) (the two negatively charged amino acids at neutral pH). Fourth, if there are at least 0.4*n occurrences of Glu and/or Asp in the n residues, the sequence is cataloged as a negatively charged amino acid sequence motif. If, however, fewer than 0.4*n occurrences of negatively charged amino acid residues are found, the sequence beginning with the first amino acid residue is discarded and the process is begun anew, for example, at a second amino acid residue immediately adjacent to the first amino acid residue. After cataloging a motif, the process can begin anew at a second amino acid residue.

The process for identifying a positively charged sequence motif is analogous to searching protein sequence data for an n residue-long amino acid sequence comprising only amino acid residues that are neutral or positively charged, and for which the magnitude of the net charge of the amino acid residue side chains at neutral pH is greater than or equal to 0.4*n.

Also analogous is the process for identifying a negatively charged amino acid sequence motif or a positively charged amino acid sequence motif of length n, allowing both positively and negatively charged amino acid residues in the motif. For example, the procedure for identifying a positively charged amino acid sequence motif of length n would be to select a first amino acid residue in a polypeptide. Next, examine this amino acid residue and the following n−1 amino acid residues for occurrences of residues that are positively or negatively charged at pH 7. Determine the net charge of the n amino acid residue side chains. If the absolute value of the net charge is less than 0.4*n, then the sequence is discarded and a new search is begun at another amino acid, while if the absolute value of the net charge is greater than or equal to 0.4*n, then the sequence is an amino acid sequence motif. The motif will be positive if net charge is greater than zero and negative if the net charge is less than zero.

De novo design of amino acid sequence motifs as presently defined follows essentially similar rules, except that the sequences are not limited to those found in nature. A length of motif n and a desired sign and magnitude of net charge are chosen. Then, n amino acids are selected for the amino acid sequence motif that result in the desired sign and magnitude of charge, so that the absolute value of the net charge of the n amino acids is greater than or equal to 0.4*n. A potential advantage of de novo design of an amino acid sequence motif is that the practitioner can select from among all amino acids (the 20 naturally occurring ones and all non-natural amino acids) to achieve the desired net charge, rather than being limited to the amino acids found in a particular known protein sequence. The larger pool of amino acids enlarges the potential range of physical, chemical and/or biological characteristics that can be selected in designing the sequence of the motif compared to identification of an amino acid sequence motif in a genomic sequence.

A designed polypeptide as presently defined will comprise one or more amino acid sequence motifs. The same motif may be repeated, or different motifs may be joined in designing a polypeptide for ELBL. In one embodiment, the amino acid sequence motifs are covalently joined with no intervening sequence. In another embodiment, a designed polypeptide comprises two or more amino acid sequence motifs covalently joined by a linker. The linker can be amino acid based, e.g., one or more amino acid residues such as glycine or proline, or it can be any other compound suitable for covalently linking two amino acid sequence motifs. In one embodiment, a linker comprises 1-4 amino acid residues, for example, 1-4 glycine and/or proline resides. The linker comprises a suitable length or composition so that the designed polypeptide is maintained at a magnitude of net charge per residue that is greater than or equal to 0.4.

In one embodiment, a designed polypeptide is greater than or equal to 15 amino acid residues long. In other embodiments, a designed polypeptide is greater than 18, 20, 25, 30, 32 or 35 amino acids long. 1,000 residues is a practical upper bound on polypeptide length.

Once amino acid sequence motifs have been selected or designed de novo, a designed polypeptide with amino acid-based linkers is synthesized using methods well known in the art, such as solid phase synthesis and F-moc chemistry, or heterologous expression in bacteria following gene cloning and transformation. Designed polypeptides may be synthesized by a peptide synthesis company, for example, SynPep Corp. (Dublin, Calif.), produced in the laboratory using a peptide synthesizer, or produced by recombinant DNA methods. Any development of novel methods of peptide synthesis could enhance the production of peptides but would not fundamentally change peptide design as described herein.

A method of making a polyelectrolyte multilayer film comprises depositing a plurality of layers of oppositely charged polyelectrolytes on a substrate. In one embodiment, at least one polyelectrolyte comprises a polypeptide such as a charged homopolypeptide or a designed polypeptide. Successively deposited polyelectrolytes will have opposite net charges. FIG. 1 is a schematic illustrating ELBL deposition. In one embodiment, deposition of a designed polypeptide (or other polyelectrolyte) comprises exposing the substrate to an aqueous solution comprising a designed polypeptide (or other polyelectrolyte) at a pH at which it has a suitable net charge for ELBL. In other embodiments, the deposition of a designed polypeptide or other polyelectrolyte on the substrate is achieved by sequential spraying of solutions of oppositely charged polypeptides. In yet other embodiments, deposition on the substrate is by simultaneous spraying of solutions of oppositely charged polyelectrolytes.

In the ELBL method of forming a multilayer film, the opposing charges of the adjacent layers provide the driving force for assembly. It is not critical that polyelectrolytes in opposing layers have the same net linear charge density, only that opposing layers have opposite charges. One standard film assembly procedure for deposition includes forming aqueous solutions of the polyelectrolytes at a pH at which they are ionized (i.e., pH 4-10), providing a substrate bearing a surface charge, and alternating immersion of the substrate into the charged polyelectrolyte solutions. The substrate is optionally washed in between deposition of alternating layers.

The concentration of polyelectrolyte suitable for deposition of the polyelectrolyte can readily be determined by one of ordinary skill in the art. An exemplary concentration is 0.1 to 10 mg/mL. Typically, the thickness of the layer produced is substantially independent of the solution concentration of the polyelectrolyte during deposition in the stated range. For typical non-polypeptide polyelectrolytes such as poly(acrylic acid) and poly(allylamine hydrochloride), layer thicknesses are about 3 to about 5 Å, depending on the ionic strength of solution. Short polyelectrolytes often form thinner layers than long polyelectrolytes. Regarding film thickness, polyelectrolyte film thickness depends on humidity as well as the number of layers and composition of the film. For example, PLL/PLGA films 50 µm thick shrink to 1.6 nm upon drying with nitrogen. In general, films of 1 µm to 100 µm or more in thickness can be formed depending on the hydration state of the film and the molecular weight of the polyelectrolytes employed in the assembly.

In addition, the number of layers required to form a stable polyelectrolyte multilayer film will depend on the polyelectrolytes in the film. For films comprising only low molecular weight polypeptide layers, a film will typically have 4 or more bilayers of oppositely charged polypeptides. For films comprising high molecular weight polyelectrolytes such as poly(acrylic acid) and poly(allylamine hydrochloride), films comprising a single bilayer of oppositely charged polyelectrolyte can be stable.

As disclosed herein, one or more polyelectrolytes are deposited on the substrate in the presence of a polymeric precipitant, typically in aqueous solution at pH 4 to 10. The use of a polymeric precipitant, for example, advantageously minimizes the loss of bioactive molecules contained within the multilayer film.

For a given set of deposition conditions, the amount of a polymeric precipitant of a particular molecular weight can be chosen to minimize loss of bioactive molecules adsorbed to a template without making the viscosity of the deposition solution unsuitable for the particular deposition process. In general, a suitable concentration of polymeric precipitant will depend on the molecular structure of the precipitant and its molecular weight. In general, the higher the concentration of polymeric precipitant, the higher the insolubility of macromolecule. Representative practical values of polymeric precipitant concentration can be given as follows: for PEG of molecular weight 3500 to 4000 Da or PPG of molecular weight 425 Da or PVA of molecular weight 5000 Da or PEI of molecular weight 40 to 60 kDa, 5-15% by weight. PEG of 300 Da is considerably more soluble than PEG of 3500-4000 Da; the former can be soluble in aqueous solution up to about 50% by weight. The maximum useful concentration of a particular precipitant will decrease in relation to an increase in concentration of a co-precipitant; for instance, a useful concentration of PEG 300 will be lower if PVA is present. If the polymeric precipitant and peptide solution is too viscous, it will not be possible to control how well it sprays. With respect to LBL methods, viscosity can affect the rate of diffusion of the polyelectrolytes in the deposition solutions, slowing down the film assembly process. The balance under any particular set of deposition conditions between the effect on the retention of the adsorbed bioactive molecule and on the viscosity of the deposition solutions can be weighed for determining the concentration and molecular weight of other polymers useful as a polymeric precipitant.

For the example of PEG as a polymeric precipitant, solution concentrations of up to about 50% (v/v) of PEG 300 can be used throughout the temperature range where the solution remains in the liquid state, nominally about 0 to about 100° C. for pure water at about 1 atm pressure. A somewhat broader temperature range may be employed when the precipitant is present in solution and the functional activity of the bioactive molecule is not irreversibly inactivated. The concentration of a particular molecular weight of PEG that can be effective in these methods at a given set of deposition conditions is determined at least in part by the maintenance of an appropriate solution viscosity.

In one embodiment, the multilayer film or microcapsule comprises a bioactive molecule. In one embodiment, the bioactive molecule is co-deposited with one or more polyelectrolyte layers. In another embodiment, the substrate comprises the bioactive molecule. For example, the substrate can be a template comprising liquid or crystalline bioactive molecules, such as drugs or proteins. In another embodiment, the substrate is coated with the bioactive molecule. For example, an inert core such as a $CaCO_3$ particle can be coated with the bioactive molecule prior to deposition of polyelectrolyte layers. The $CaCO_3$ particle can be removed after polyelectrolyte deposition to form a hollow microcapsule comprising the bioactive molecule.

In one embodiment, the polymeric precipitant has a favorable effect on deposition of polyelectrolyte in making the film, as well as decreasing the solubility of an adsorbed bioactive molecule, thereby increasing the amount of material encapsulated. A suitable assay to measure loss of the bioactive molecules from the template can be used in making an empirical determination of the appropriate concentration of a given polymeric precipitant. For example, the bioactive molecule can be labeled with a fluorescent group such as fluorescein or CY3, a fluorescent cyanine compound (Amersham BioSciences), or with a group with a characteristic absorbance spectrum such as tyrosine. Assays to determine fluorescence or absorption retained with the template can be performed to evaluate retention of the bioactive molecule in the presence or absence of a particular concentration of a given polymeric precipitant.

The invention further includes the film made by this method. It is possible that some polymeric precipitant will become incorporated into the film the fabrication process. In some cases, such incorporation might be desirable or useful.

In another aspect, methods of improving bioactive molecule retention during fabrication of a polyelectrolyte multilayer film are provided. In some embodiments, the method comprises depositing a plurality of layers of oppositely charged polyelectrolytes on a substrate comprising a bioactive molecule, wherein deposition of one or more of the oppositely charged polyelectrolytes is performed in the presence of a polymeric precipitant. In one embodiment, one or more of the polyelectrolytes comprises a polypeptide. In other embodiments, the method comprises adsorbing a bioactive molecule onto a substrate; and depositing a plurality of layers of oppositely charged polyelectrolytes on the bioactive molecule-coated substrate. Deposition of one or more of the oppositely charged polyelectrolytes and/or the adsorption of the bioactive molecule is performed in the presence of a polymeric precipitant. The amount of the bioactive molecule retained during deposition of a layer of a polyelectrolyte in the presence of a polymeric precipitant relative to the amount retained in the absence of the polymeric precipitant is improved by at least 15%, at least 30%, at least 50%, at least 67%, at least 100%, or at least 200%.

In some embodiments, the deposition of the oppositely charged polyelectrolytes is by LBL deposition from aqueous solution. In other embodiments, the deposition of the oppositely charged polyelectrolytes on the substrate is by simultaneous spraying of solutions of the oppositely charged polyelectrolytes. In some embodiments, an oppositely charged polyelectrolyte deposited on the template comprises an amino acid sequence motif wherein the amino acid sequence motif comprises n amino acids and the balance of charges of the same charge in the amino acid motif is greater than or equal to 0.4*n. In other embodiments, at least one of the oppositely charged polypeptides comprises PLL or PLGA.

The bioactive molecule is, for example, a protein, an oligopeptide, a nucleic acid, an oligonucleotide, a lipid, a carbohydrate, a pharmaceutical, an antimicrobial agent, a membrane structure, a cell, a virus, a tissue, or a combination thereof. The protein can be an enzyme. In some embodiments, the enzyme is glucose oxidase.

In some embodiments, the bioactive molecule is deposited on a template. Suitable templates include an organic substrate and/or an inorganic substrate. The template can comprise a material that can be dissolved or disintegrated by changing a chemical or physical property of the substrate or the solution containing the template. For example, in some embodiments, the template comprises a $CaCO_3$ microparticle, which can be dissolved by mixing with EDTA. In other embodiments, the template is a crystalline bioactive molecule such as a protein or a drug.

This aspect of the invention further provides a polypeptide film retaining a bioactive molecule made by these methods.

The invention is further illustrated by the following non-limiting examples.

EXAMPLE 1

Glucose Oxidase (GOx) Adsorption on $CaCO_3$ and MF Particles

Figure 2:
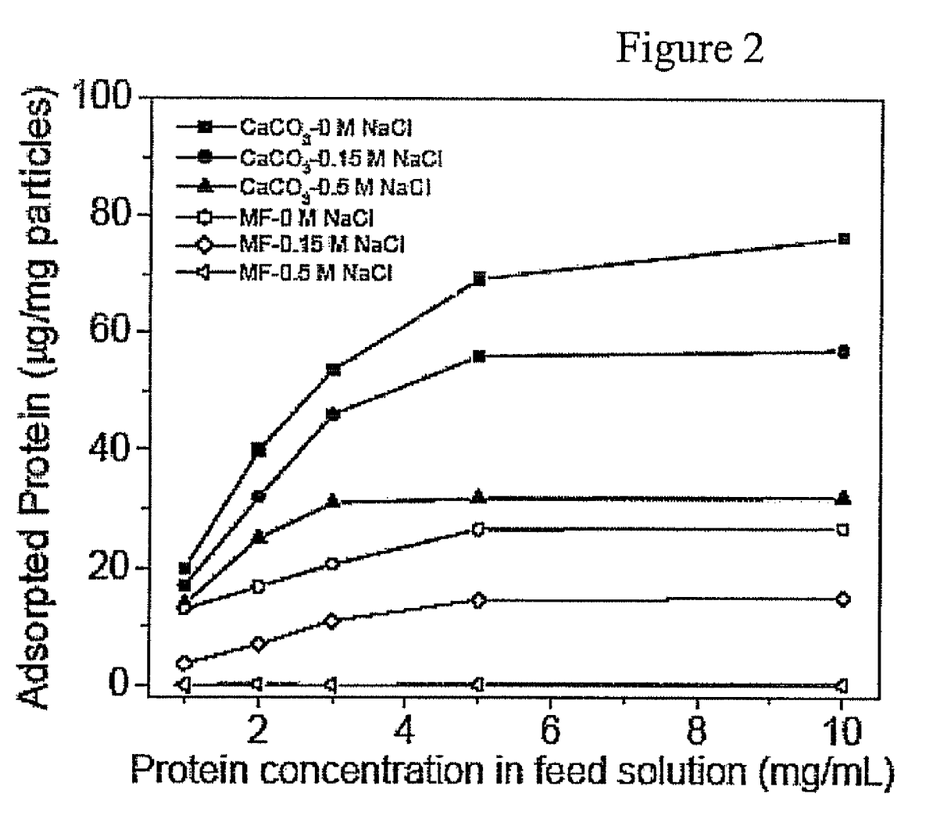
FIG. 2 shows the adsorption capacity of glucose oxidase (GOx) onto $CaCO_3$ or melamine formaldehyde (MF) particle templates as a function of the concentration of the enzyme and concentration of NaCl.

The model protein was GOx, chosen for its useful enzymatic properties. For GOx adsorption experiments, 5 mg of $CaCO_3$ particles (PlasmChem GmbH, Germany) or melamine formaldehyde (MF) particles were mixed with 100 µL of 37,300 units/g Type II-S GOx from *A. niger* (SIGMA, USA) in 10 mM Tris buffer, pH 7.4. Adsorption of GOx can be performed at a temperature where the GOx solution remains in the liquid state, nominally about 0 to about 100° C. for pure water at about 1 atm pressure, and GOx enzymatic activity is not irreversibly inactivated. The final particle concentration was 5% (w/v). Enzyme adsorption onto microparticles was quantified by decrease in absorbance of the liquid phase at 280 nm using a Jasco V-430 spectrophotometer (Japan). GOx-loaded microparticles were separated from the polypeptide adsorption solution by centrifugation. Adsorption to the particles as a function of GOx concentration and salt concentration in the feed solution is shown in FIG. 2. The maximum amount of GOx loaded onto $CaCO_3$ particles was about 76 µg/mg particles, or about $9.4 \times 10^{-12}$ gram of enzyme per particle, assuming a particle volume of $4.6 \times 10^{-11}$ $cm^3$. FIG. 2 shows that maximal adsorption to either template was achieved in the absence of added monovalent salt under these deposition conditions.

EXAMPLE 2

Encapsulation of an Enzyme in Polypeptide Microcapsules

Poly(L-lysine) (PLL) (W about 14.6 lcDa) and poly(L-glutamic acid) (PLGA) (MW about 13.6 kDa) were selected as the oppositely charged polypeptide for deposition of layers in this encapsulation pilot study because they are readily available from a commercial source. Encapsulation involving designed polypeptides in place of PLL and/or PLGA would be analogous. An example of a pair of oppositely charged peptides that have used for this purpose is given in Li and Haynie (2004) *Biomacromolecules* 5:1667-1670.

GOx was adsorbed to $CaCO_3$ microparticles by adding 0.10 mL of 5 mg/mL GOx solution to 5 mg of $CaCO_3$ microparticles, mixing thoroughly for 2 hours, and centrifuging for 5 minutes at 1000×g for removal of the fluid phase.

Deposition of each polypeptide multilayer on GOx-adsorbed $CaCO_3$ microparticles involved self-assembly for 10 minutes under gentle shaking at 4° C., followed by centrifugation to separate particles from unbound peptide in the fluid phase. A volume of 0.1 mL of either a 1 mg/mL solution of PLL (W about 14.6 kDa) or of PLGA (MW about 13.6 kDa) in 10 mM Tris, 0.5 M NaCl, pH 7.4 was added to the microparticles at 4° C. and mixed thoroughly. Alternating layers of PLL and PLGA were deposited on the microparticles. Up to 50% (v/v) PEG 300 (Fluka) was present in the polypeptide solutions; higher average molecular mass PEG tended to give an overly viscous solution for the purpose. After separation of the fluid phase from particles following each polypeptide adsorption step, assembly solution supernatants were analyzed for aromatic absorbance. PLL and PLGA contain no aromatic residues and therefore do not absorb at 280 nm; GOx does absorb at this wavelength. Two intermediate washing steps were carried out with deionized water at 4° C. between polypeptide assembly cycles. This process was repeated until the desired number of layers was deposited (typically 6 bilayers). After assembly of the final layer of polypeptide, coated particles were rinsed and collected by centrifugation. Particle cores were then dissolved by treatment with 0.2 M EDTA, pH 7.4. The dissolution process took 10-20 minutes. Microcapsules were collected by centrifugation at 2000×g for 5 minutes, rinsed with deionized water, and re-suspended in 0.25 mL 10 mM Tris buffer. Aliquots of sample were assayed for enzyme activity as described below. The concentration of sample used for further experiments was estimated to be $1.5 \times 10^8$ capsules/mL. The same procedure was followed for the confocal fluorescence experiments shown in FIG. 7, except that Cy3-labeled GOx replaced GOx.

Figure 3:
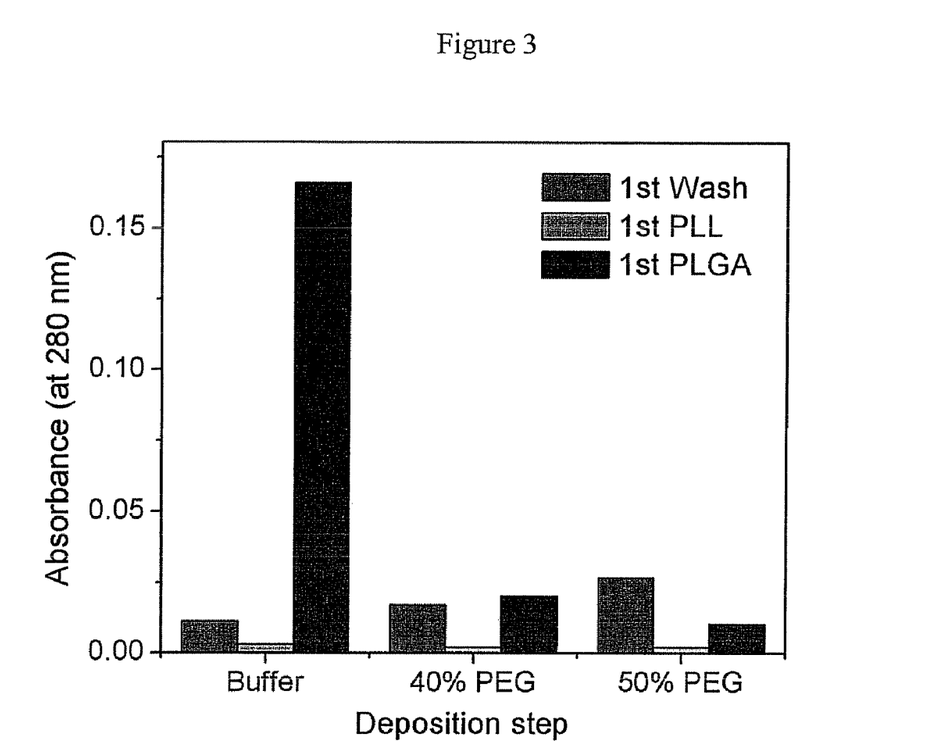
FIG. 3 shows the loss of adsorbed GOx from $CaCO_3$ templates during deposition of an encapsulating poly(L-lysine)/poly(L-glutamic acid) (PLL/PLGA) film as absorbance at 280 nm due to the released GOx present in the wash, assembly buffer of poly(L-lysine) (PLL), or assembly buffer of poly(L-glutamic acid) (PLGA) in the absence of a polymeric precipitant, in the presence of 40% PEG 300, or in the presence of 50% PEG 300.

FIG. 3 shows loss of adsorbed GOx from $CaCO_3$ templates during deposition of an encapsulating PLL/PLGA film as absorbance at 280 nm due to the released GOx present in the wash, assembly buffer of PLL, and assembly buffer of PLGA for assembly in buffer in absence of a polymeric precipitant, assembly in buffer in the presence of 40% PEG 300, and for assembly in buffer in presence of 50% PEG 300. The magnitude of the absorbance at 280 nm released during deposition of the first PLGA layer in the presence of 40% or 50% PEG 300 is significantly less than that observed in the absence of PEG 300. Increasing the concentration of PEG 300 from 10% up to 50% in the deposition buffers was found to decrease desorption of the GOx from the template during film assembly.

Concentrations of PEG 8000 comparable to those investigated for PEG 300 yielded solution viscosities in which self-assembly of the polypeptide layers was not time-effective. Molecular weights of PEG that are liquid at room temperature, as is PEG 300, are suitable for use at 4° C. as the polymeric precipitant.

Figure 4:
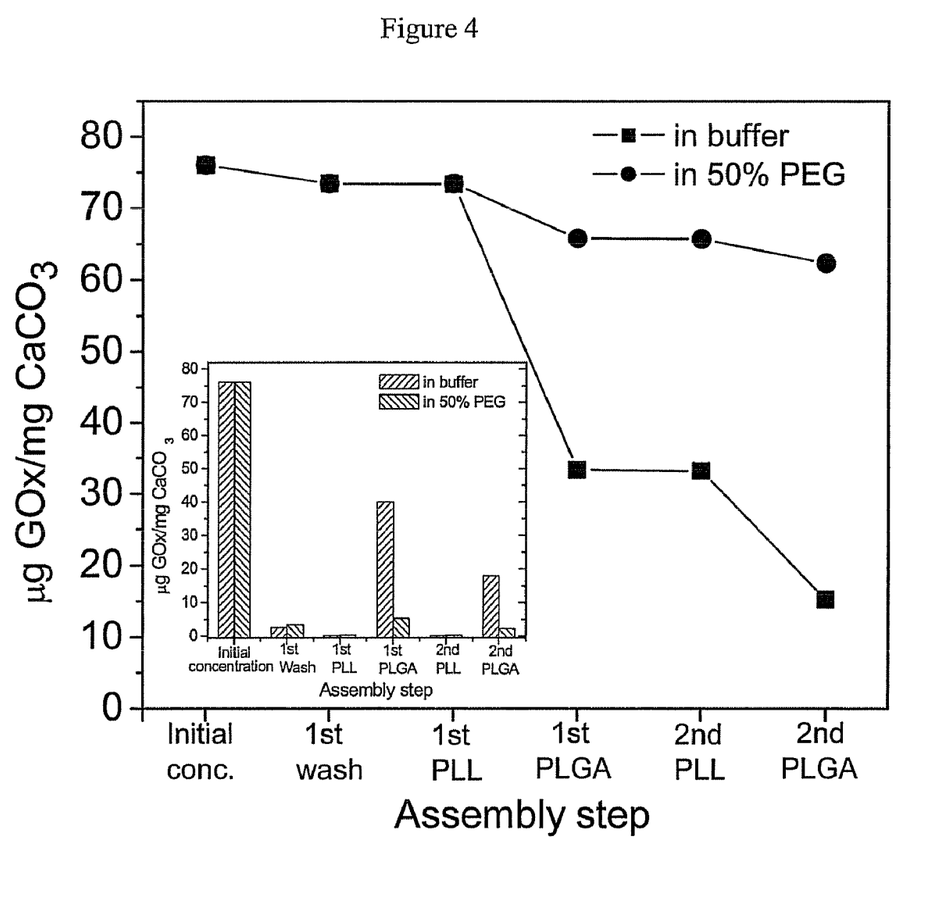
FIG. 4 shows the retention of GOx on $CaCO_3$ templates during deposition of an encapsulating (PLL)/(PLGA) film in the presence or absence of 50% PEG 300 in the deposition solutions.

FIG. 4 shows retention of GOx on $CaCO_3$ templates during deposition of the encapsulating PLL/PLGA film. The first points represent initial GOx "loading" on templates. Succeeding points show remaining GOx on the templates in subsequent peptide assembly and particle rinsing steps. Only two deposition cycles are shown. Inset, complementary data showing the release of GOx from GOx-loaded template particles as measured in the supernant of washing and assembling solutions.

Figure 5:
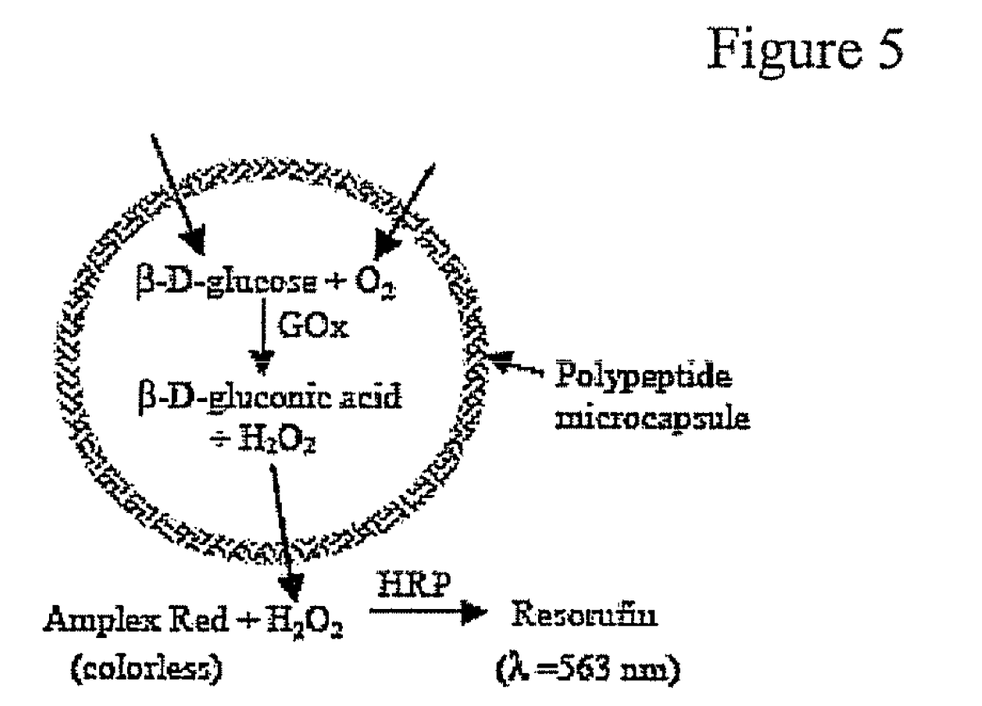
FIG. 5 shows the reaction scheme for photometric measurement of GOx activity in a polypeptide microcapsule.

A calorimetric enzyme-coupled assay involving Amplex Red as substrate was used to quantitate GOx activity. FIG. 5 shows a reaction scheme for the assay. Glucose and oxygen diffuse inside the capsule for use by GOx to produce glucoronic acid and $H_2O_2$. $H_2O_2$ diffuses out of the capsule and is detected, indirectly, by Amplex Red. Initially colorless, this reagent is oxidized by $H_2O_2$ in the presence of horseradish peroxidase (HRP) (250-330 units/mg solid), forming resorufin, which can be detected by absorbance at $\lambda=563$ nm. The following stock solutions were prepared: 10 mM Amplex Red reagent (Molecular Probes, USA) in DMSO, 10 U/mL HRP in 50 mM phosphate buffer and 0.15 M NaCl (PBS), 400 mM glucose in 50 mM PBS, and 100 U/mL GOx in 50 mM PBS. A working solution was prepared by mixing three solutions: 30 μL Amplex Red, 75 μL HRP, and 450 μL glucose. Standard solutions of GOx, each 500 μL and containing 0 to 10 mU/mL, were prepared by diluting the 100 U/mL GOx stock solution. Capsule samples and control samples without GOx each were diluted to 500 μL with 50 mM PBS buffer. A reaction was initiated by adding 40 μL Amplex Red/HRP/glucose working solution to tubes representing standards, controls, and capsule samples. Reaction mixtures were incubated for 30 minutes in the dark at ambient temperature with gentle agitation. Absorbance of resorufin was measured at 563 nm. The measured enzymatic activity was converted to amount of active GOx by calibrating the measurement of the activity relative to that of a known quantity of GOx.

Figure 6:
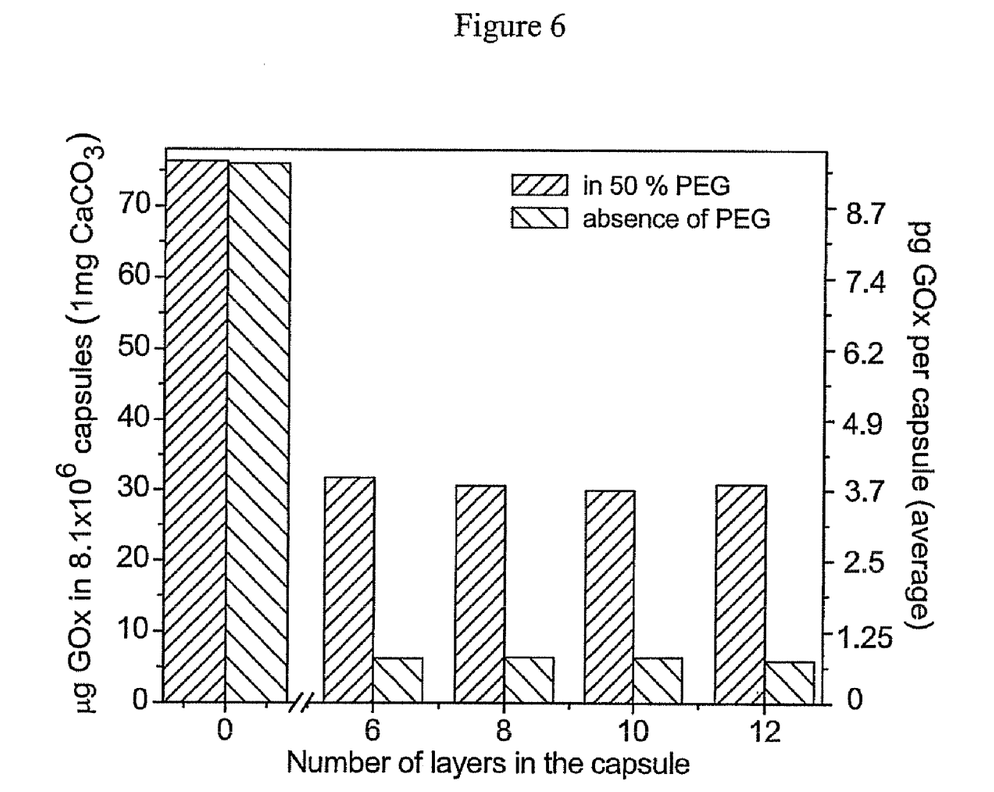
FIG. 6 shows the measured activity of encapsulated GOx as a function of number of layers of polypeptide.

FIG. 6 shows amount of active encapsulated GOx as a function of number of layers of polypeptide determined using the enzymatic assay. The amount of material retained in the capsule after template dissolution is shown, with and without addition of PEG in the polypeptide assembly solutions. Capsules of fewer than 6 layers were unstable in solution. As shown in FIG. 6, when polypeptide assembly was carried out in the absence of PEG, GOx activity associated with microparticles decreased markedly on deposition of PLL/PLGA up to 2 bilayers. Measured activity tended to reach a constant value (e.g., about 11% of the value prior to deposition of polypeptide) independent of the number of layers in the 3-6 bilayer range. Addition of PEG to the PLL and the PLGA assembly solutions substantially improved the "loading" of polypeptide-based "artificial cells" with GOx. About 70% of enzyme activity was retained in the cells after deposition of 6 bilayers but prior to phase separation. Sonication for 20 min of 6-bilayer cells assembled using PEG resulted in no decrease in enzyme activity. This suggests that encapsulation of GOx by a polypeptide multilayer film neither inhibited enzyme activity nor prevented diffusion of small molecules (e.g. glucose (enzyme substrate) and reaction products) across the barrier. The extent of migration of GOx into the artificial cell wall was not determined.

Confirmation that measured enzyme activity was in fact associated with artificial cells was obtained as follows. GOx activity in solution was quantified after separation of the 6-bilayer cells from the fluid phase using a 0.22 μm filter. No GOx activity was detected in the filtrate in the absence of PEG; the enzyme activity was in the artificial cells. Some enzyme (about $1.5 \times 10^{-12}$ g/capsule) was detected in the filtrate when the PEG protocol was used. Presumably this was due to partial collapse of the coated templates/cells during repeated centrifugation and washing. No further activity was detected in the filtrate after re-suspension of the cells, indicating that loaded GOx did not leach out. The same approach was used to quantify retention of GOx in cells.

Figure 7:
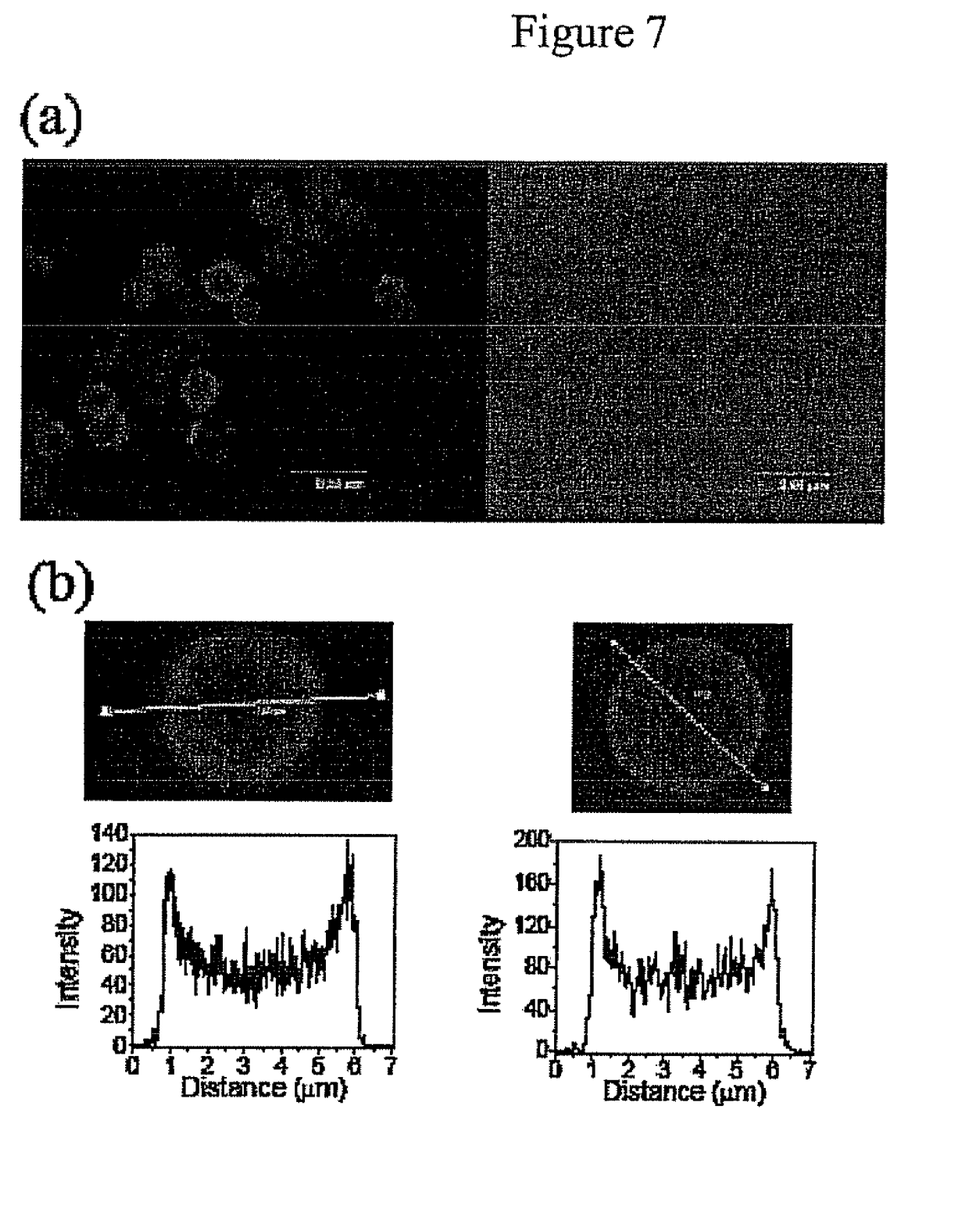
FIG. 7 shows (a) Confocal microscopy image of microcapsules after dissolution of template. Left, fluorescence; right, brightfield. (b) Fluorescence intensity profile of a capsule. Left, loaded capsule; right, coated core prior to dissolution of template.

GOx was labeled with a fluorescent dye, Cy3 mono-reactive NHS-ester (Amersham Biosciences, UK) to visualize GOx-loaded microcapsules. Encapsulation of Cy3-GOx within a PLL/PLGA film followed adsorption onto $CaCO_3$ microparticles. Study of influence of layer number on artificial cell stability by fluorescence microscopy revealed that coatings with fewer than 3 bilayers tended to dissociate after core particle dissolution, whereas capsules with 3 or more bilayers usually were stable in aqueous solution on a time scale of weeks. This is consistent with the GOx activity measurements reported here. Film thickness is directly related to layer number. Further evidence of loading of Cy3-labeled GOx into PLL/PLGA 6-bilayer microcapsules was obtained by confocal laser fluorescence microscopy (FIG. 7a, left panel). The right panel, obtained by brightfield illumination, shows that the microparticle templates were completely dissolved by treatment with EDTA. Fluorescence intensity cross-sectional profiles of a 6-bilayer capsule revealed that the microcapsule interior was filled with a substantial quantity of unbound Cy3-labeled GOx (FIG. 7b, left). The diameter of the cell was approximately that of the original template (FIG. 7b, right). The appearance of two peaks in the intensity profile indicates that some GOx was bound to the cell "membranes," probably due to electrostatic attraction and dissipation. Further evidence of GOx encapsulation in polypeptide cells was obtained by circular dichroism spectroscopy (data not shown).

EXAMPLE 3

Encapsulation of an Enzyme in a Polyelectrolyte Microcapsule

In another example, the protein hemoglobin is loaded onto calcium carbonate particles in phosphate buffered saline (pH 7.4) and encapsulated with non-peptide polyelectrolytes. Protein loading efficiency is increased by the addition of a polymeric precipitant to the protein solution, for example, 40% PEG 300. The adsorbed protein is encapsulated by LBL with two oppositely charged polyelectrolytes. Polymers suitable for the purpose are poly(styrene sulfonate), a polyanion, and poly(allylamine), a polycation. Proof of protein loading may be obtained by spectrophotometry in the visible range: Hemoglobin has a large absorption band near 410 nm, due to the presence of heme.

This invention presents a means of high-efficiency retention of functional bioactive molecules in nanoengineered polyelectrolyte films and microcapsules by inclusion of a polymeric precipitant in assembly buffers. The polyelectrolyte multilayer film was semipermeable, preventing leakage of the model biologic without precluding the permeability of small molecules. The inherent biocompatibility of the encapsulating polypeptides presents advantages for biomedical applications over non-biodegradable synthetic polyelectrolytes more commonly used in forming thin films by LBL.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

We claim:

1. A method of making a film, the method comprising:
   depositing a first layer polyelectrolyte on a surface of a substrate to form a first layer; and
   depositing a second layer polyelectrolyte on the first layer polyelectrolyte to form a second layer;
   wherein a bioactive molecule is co-deposited with the first layer polyelectrolyte, second layer polyelectrolyte, or both, or wherein the substrate comprises a bioactive molecule;
   wherein the first layer polyelectrolyte, the second layer polyelectrolyte, or both, is deposited using a solution comprising a polymeric precipitant at a concentration to improve retention of the bioactive molecule;
   wherein the polymeric precipitant, the first layer polyelectrolyte and the second layer polyelectrolyte are different; and
   wherein the first layer polyelectrolyte and the second layer polyelectrolyte have net charges of opposite polarity.

2. The method of claim 1, wherein the first layer polyelectrolyte, the second layer polyelectrolyte, or both, comprises a designed polypeptide, wherein
   the designed polypeptide comprises one or more first amino acid sequence motifs,
      wherein the one or more amino acid sequence motifs consists of 5 to 15 amino acid residues and has a magnitude of net charge per residue of greater than or equal to 0.4, and
   wherein the designed polypeptide is not a homopolypeptide, is at least 15 amino acid residues long, and has a magnitude of net charge per residue of greater than or equal to 0.4.

3. The method of claim 1, wherein the substrate comprises a bioactive molecule.

4. The method of claim 3, wherein the bioactive molecule is in the form of a coating on the substrate.

5. The method of claim 4, wherein the substrate comprises a template suitable for disintegration after polyelectrolyte multilayer film deposition.

6. The method of claim 5, wherein the bioactive molecule is in the form of a core.

7. The method of claim 1, further comprising depositing a bioactive molecule onto the surface of the substrate prior to depositing the first layer polyelectrolyte.

8. The method of claim 1, wherein the polymeric precipitant comprises polyethylene glycol, polyacrylic acid, polyvinyl alcohol, polyvinylpyrrolidone, polypropylene glycol, or a combination of one or more of the foregoing polymeric precipitants.

9. The method of claim 1, wherein the film is in the form of a microcapsule.

10. The method of claim 9, wherein a bioactive molecule is encapsulated by the microcapsule.

11. A method of improving bioactive molecule retention during fabrication of a polyelectrolyte multilayer film, the method comprising;
    depositing a first layer polyelectrolyte on a surface of a substrate to form a first layer; and
    depositing a second layer polyelectrolyte on the first layer polyelectrolyte to form a second layer;
    wherein the substrate comprises a bioactive molecule;

wherein the first layer polyelectrolyte, the second layer polyelectrolyte, or both, is deposited on the substrate using a solution comprising a polymeric precipitant at a concentration to improve retention of the bioactive molecule;

wherein the polymeric precipitant, the first layer polyelectrolyte and the second layer polyelectrolyte are different; and wherein the first layer polyelectrolyte and the second layer polyelectrolyte have net charges of opposite polarity.

12. The method of claim 11, wherein the first layer polyelectrolyte, the second layer polyelectrolyte, or both, comprises a designed polypeptide, wherein the designed polypeptide comprises one or more first amino acid sequence motifs, wherein the one or more amino acid sequence motifs consists of 5 to 15 amino acids and has a magnitude of net charge per residue of greater than or equal to 0.4, and wherein the designed polypeptide is not a homopolypeptide, is at least 15 amino acid residues long, and has a magnitude of net charge per residue of greater than or equal to 0.4.

13. The method of claim 11, further comprising depositing a bioactive molecule onto the surface of the substrate prior to depositing the first layer polyelectrolyte.

14. The method of claim 11, wherein the bioactive molecule is in the form of a coating on the substrate.

15. The method of claim 11, wherein the substrate comprises a template suitable for disintegration after polyelectrolyte multilayer film deposition.

16. The method of claim 11, wherein the bioactive molecule is in the form of a core.

17. A method of making a film, the method comprising:
depositing a bioactive molecule on the surface of a substrate in the presence of a polymeric precipitant;
depositing a first layer polyelectrolyte on a surface of the substrate to form a first layer; and
depositing a second layer polyelectrolyte on the first layer polyelectrolyte to form a second layer;
wherein the first layer polyelectrolyte and the second layer polyelectrolyte have net charges of opposite polarity,
wherein the first layer polyelectrolyte, the second layer polyelectrolyte, or both, is deposited on the substrate using a solution comprising a polymeric precipitant at a concentration to improve retention of the bioactive molecule;
and wherein both polymeric precipitants, are different from the first layer polyelectrolyte and the second layer polyelectrolyte.

18. The method of claim 17, wherein the substrate comprises a template suitable for disintegration after polyelectrolyte multilayer film deposition.

19. A method of making a film, the method comprising:
depositing a first layer polyelectrolyte on a surface of a substrate to form a first layer; and
depositing a second layer polyelectrolyte on the first layer polyelectrolyte to form a second layer;
wherein the first layer polyelectrolyte, the second layer polyelectrolyte, or both, is deposited on the substrate using a solution comprising a polymeric precipitant;
wherein the polymeric precipitant comprises polyethylene glycol, polyacryclic acid, polyvinyl alcohol, polyvinylpyrrolidone, polypropylene glycol, or a combination of one or more of the foregoing polymeric precipitants;
wherein the first layer polyelectrolyte, the second layer polyelectrolyte and polymeric precipitant are different; and
wherein the first layer polyelectrolyte and the second layer polyelectrolyte have net charges of opposite polarity.

20. The method of claim 1, wherein the first layer polyelectrolyte, the second layer polyelectrolyte, or both, is deposited in the presence of a bioactive molecule.

* * * * *

UNITED STATES PATENT AND TRADEMARK OFFICE
CERTIFICATE OF CORRECTION

PATENT NO. : 7,662,911 B2
APPLICATION NO. : 11/559175
DATED : February 16, 2010
INVENTOR(S) : Haynie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,911 B2 | Page 1 of 1 |
| APPLICATION NO. | : 11/559175 | |
| DATED | : February 16, 2010 | |
| INVENTOR(S) | : Donald T. Haynie and Zheng-liang Zhi | |

It is certified that error appears in the above-identified patent and that said Letters Patent is hereby corrected as shown below:

In column 1 line 8 insert the following:

--FEDERALLY SPONSORED RESEARCH OR DEVELOPMENT:

This invention was made with government support under DMI-0403882 awarded by the National Science Foundation. The U.S. government has certain rights in the invention.--

Signed and Sealed this
Sixth Day of March, 2012

David J. Kappos
*Director of the United States Patent and Trademark Office*